US012558396B2

(12) United States Patent
Jung et al.

(10) Patent No.: US 12,558,396 B2
(45) Date of Patent: \*Feb. 24, 2026

(54) USE OF CYCLO(HIS-PRO) (CHP) FOR PREVENTING, ALLEVIATING OR TREATING PERITONEAL FIBROSIS

(71) Applicants: NOVMETAPHARMA CO., LTD., Seoul (KR); SEOUL NATIONAL UNIVERSITY R&DB FOUNDATION, Seoul (KR); SEOUL NATIONAL UNIVERSITY HOSPITAL, Seoul (KR)

(72) Inventors: Hoe Yune Jung, Pohang-si (KR); Do Hyun Lee, Pohang-si (KR); Heon Jong Lee, Incheon (KR); Yon Su Kim, Seoul (KR); Seung Hee Yang, Seoul (KR)

(73) Assignees: NOVMETAPHARMA CO., LTD., Seoul (KR); SEOUL NATIONAL UNIVERSITY HOSPITAL, Seoul (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 1118 days.

This patent is subject to a terminal disclaimer.

(21) Appl. No.: 17/599,118

(22) PCT Filed: Mar. 30, 2020

(86) PCT No.: PCT/KR2020/004343
§ 371 (c)(1),
(2) Date: Sep. 28, 2021

(87) PCT Pub. No.: WO2020/197356

PCT Pub. Date: Oct. 1, 2020

(65) Prior Publication Data
US 2022/0193179 A1       Jun. 23, 2022

(30) Foreign Application Priority Data

Mar. 28, 2019    (KR) ........................ 10-2019-0036269
Mar. 27, 2020    (KR) ........................ 10-2020-0037858

(51) Int. Cl.
| | |
|---|---|
| *A61K 38/01* | (2006.01) |
| *A23L 33/18* | (2016.01) |
| *A61K 38/12* | (2006.01) |
| *A61P 1/16* | (2006.01) |
| *A61P 11/00* | (2006.01) |
| *A61P 19/04* | (2006.01) |
| *A61P 43/00* | (2006.01) |

(52) U.S. Cl.
CPC ............ *A61K 38/011* (2013.01); *A23L 33/18* (2016.08); *A61K 38/12* (2013.01); *A61P 1/16* (2018.01); *A61P 11/00* (2018.01); *A61P 19/04* (2018.01); *A61P 43/00* (2018.01)

(58) Field of Classification Search
CPC ....... A23L 33/10; A23L 33/18; A61K 38/011; A61K 38/05; A61K 38/12; A61M 1/287; A61P 1/16; A61P 11/00; A61P 19/04; A61P 43/00
See application file for complete search history.

(56) References Cited

U.S. PATENT DOCUMENTS

| | | | |
|---|---|---|---|
| 6,090,780 A | 7/2000 | Prasad | |
| 7,202,279 B1 | 4/2007 | Kozikowski et al. | |
| 10,683,300 B2 | 6/2020 | Olmstead et al. | |
| 2007/0161640 A1 | 7/2007 | Kozikowski et al. | |
| 2009/0004291 A1 | 1/2009 | Song et al. | |
| 2009/0297616 A1 | 12/2009 | Posten | |
| 2010/0144624 A1 | 6/2010 | Sinisterramillán et al. | |
| 2013/0331344 A1 | 12/2013 | Tsuruoka et al. | |
| 2020/0017509 A1 | 1/2020 | Olmstead et al. | |
| 2020/0237815 A1 | 7/2020 | Martin | |
| 2020/0345728 A1 | 11/2020 | Song et al. | |
| 2022/0193073 A1 | 6/2022 | Jung et al. | |
| 2022/0202897 A1* | 6/2022 | Jung | A23L 33/10 |

FOREIGN PATENT DOCUMENTS

| | | |
|---|---|---|
| JP | 2003-525850 A | 9/2003 |
| JP | 2004-518614 A | 6/2004 |
| JP | 2007-500747 A | 1/2007 |
| JP | 2011-521956 A | 7/2011 |
| JP | 2013-537195 A | 9/2013 |

(Continued)

OTHER PUBLICATIONS

Machine Translation of WO2018012901A1 (Year: 2018).*

(Continued)

*Primary Examiner* — Jeffrey H Murray
*Assistant Examiner* — Daniel John Burkett
(74) *Attorney, Agent, or Firm* — Sughrue Mion, PLLC

(57) ABSTRACT

A cyclo(His-Pro)(CHP) is useful for preventing, alleviating or treating peritoneal fibrosis. A pharmaceutical composition for preventing or treating peritoneal fibrosis, a dietary supplement composition for preventing or alleviating peritoneal fibrosis, and a peritoneal dialysis solution, which all contain CHP is disclosed. Also disclosed are a method for preventing or treating peritoneal fibrosis by using CHP, a peritoneal dialysis method using CHP, a use of CHP during the preparation of a pharmaceutical composition for preventing or treating peritoneal fibrosis, and/or a use of CHP in the preparation of a peritoneal dialysis solution.

8 Claims, 6 Drawing Sheets

(56) References Cited

FOREIGN PATENT DOCUMENTS

| | | | | |
|---|---|---|---|---|
| JP | 2018-510910 A | 4/2018 | | |
| JP | 2022-528087 A | 6/2022 | | |
| JP | 2022-528857 A | 6/2022 | | |
| KR | 10-2010-0014736 A | 2/2010 | | |
| KR | 10-2010-0127728 A | 12/2010 | | |
| KR | 10-2012-0055095 A | 5/2012 | | |
| KR | 10-2012-0055096 A | 5/2012 | | |
| KR | 10-2013-0006170 A | 1/2013 | | |
| KR | 10-2016-0040452 | 4/2016 | | |
| KR | 10-1617584 B1 | 5/2016 | | |
| KR | 10-1734986 B1 | 5/2017 | | |
| KR | 10-2018-0008305 A | 1/2018 | | |
| KR | 10-2133151 | 7/2020 | | |
| KR | 10-2140910 | 8/2020 | | |
| WO | 95/29675 A1 | 11/1995 | | |
| WO | 02/01956 A1 | 1/2002 | | |
| WO | 2008/109445 A1 | 9/2008 | | |
| WO | WO-2018012901 A1 * | 1/2018 | ............ | A23L 33/00 |
| WO | 2018/094023 A2 | 5/2018 | | |
| WO | 2020/013974 A1 | 1/2020 | | |

OTHER PUBLICATIONS

Zhang et. al.; "Strategies for preventing peritoneal fibrosis in peritoneal dialysis patients: new insights based on peritoneal inflammation and angiogenesis"; Front. Med., 11(3), 349-358 (Year: 2017).*

Extended European Search Report issued Aug. 29, 2024 in European Application No. 21905957.3.

Office Action issued Nov. 18, 2023 in Chinese Application No. 201980046575.8.

Silvia Grottelli et al., "The Role of Cyclo(His-Pro) in Neurodegeneration", Int. J. Mol. Sci., 2016, pp. 1-14, vol. 17, No. 1332.

Silvia Grottellia et al., "Cyclo(His-Pro) inhibits NLRP3 inflammasome cascade in ALS microglial cells", Molecular and Cellular Neuroscience, 2019, pp. 23-31, vol. 94.

A. Minelli et al., "Focus on cyclo(His-Pro): history and perspectives as antioxidant peptide", Amino Acids, 2008, pp. 283-289, vol. 35.

International Searching Authority, International Search Report of PCT/KR2020/004343 dated Jul. 17, 2020 [PCT/ISA/210].

International Search Report mailed Mar. 22, 2022 in copending Application No. PCT/IB2021/061882.

Kakkar, A.P. Drug Development and Industrial Pharmacy, 23(11), 1063-1067 (1997).

J.C. Sible, Fibronectin gene expression differs in normal and abnormal human wound healing, Wound Repair Regen., Jan. 1994, vol. 2, No. 1.

Pei-Hui Lin et al., "Zinc in Wound Healing Modulation," Nutrient, 2018, vol. 10, No. 16, pp. 1-20 (20 pages total).

Merriam-Webster online dictionary "aberrant" definition, accessed 2023, no pagination, https://www.merriam-webster.com/dictionary/aberrant.

Chao-Sheng Lo et al., "Atrial Natriuretic Peptide Attenuates High Glucose-Activated Transforming Growth Factor-β, Smad and Collagen Synthesis in Renal Proximal Tubular Cells", Journal of Cellular Biochemistry, 2008, vol. 109, pp. 1999-2009 (11 pages total).

Latha Muniappan et al., "Calpain Inhibition Attenuates Adipose Tissue Inflammation and Fibrosis in Diet-induced Obese Mice", Scientific Reports, 2017, vol. 7, No. 14398, pp. 1-15 (15 pages total).

Fumiko Nakazeki et al., "Loss of periostin ameliorates adipose tissue inflammation and fibrosis in vivo", Scientific Reports, 2018, vol. 8, No. 8553, pp. 1-14 (14 pages total).

Jeffrey E. Pessin et al., "How Does High-Fat Diet Induce Adipose Tissue Fibrosis?", Journal of Investigative Medicine, 2012, vol. 60, No. 8, pp. 1147-1150 (5 pages total).

Matteo Rosselli et al., "The Metabolic Syndrome and Chronic Liver Disease", Current Pharmaceutical Design, 2014, vol. 20, pp. 5010-5024 (15 pages total.

Simon Schenk et a., "Insulin sensitivity: modulation by nutrients and inflammation", The Journal of Clinical Investigation, 2008, vol. 118, No. 9, pp. 2992-3002 (12 pages total).

Kai Sun et al., "Adipose tissue remodeling and obesity", The Journal of Clinical Investigation, 2011, vol. 121, No. 6, pp. 2094-2101 (9 pages total).

Julien Ternacle et al., "Short-term high-fat diet compromises myocardial function: a radial strain rate imaging study", European Heart Journal—Cardiovascular Imaging, 2017, vol. 18, pp. 1283-1291 (9 pages total).

Elena Ulasova et al., "Loss of interstitial collagen causes structural and functional alterations of cardiomyocyte subsarcolemmal mitochondria in acute volume overload", Journal of Molecular and Cellular Cardiology, 2011, vol. 50, pp. 147-156 (10 pages total).

Kandy T. Velazquez et al., "miR155 deficiency aggravates high-fat diet-induced adipose tissue fibrosis in male mice", Physiological Reports, 2017, vol. 5, Issue 18, e13412, pp. 1-11 (11 pages total).

Lijun Wang et al., "Berberine alleviates adipose tissue fibrosis by inducing AMP-activated kinase signaling in high-fat diet-induced obese mice", Biomedicine & Pharmacotherapy, 2018, vol. 105, pp. 121-129 (9 pages total).

Davina Wu et al., "Eosinophils sustain adipose alternatively activated macrophages associated with glucose homeostasis", Science, 2011, vol. 332, No. 6026, pp. 243-247 (10 pages total).

Mng Xia et al., "Characterization of the inflammatory and fibrotic response in a mouse model of cardiac pressure overload", Histochem Cell Biol, 2009, vol. 131, pp. 471-481 (11 pages total).

Zhou Xu et al., "Bixin ameliorates high fat diet-induced cardiac injury in mice through inflammation and oxidative stress suppression", Biomedicine & Pharmacotherapy, 2017, vol. 89, pp. 991-1004 (14 pages total).

Yi-Chao Zhao et al., "Nuclear receptor retinoid-related orphan receptor α deficiency exacerbates high-fat diet-induced cardiac dysfunction despite improving metabolic abnormality", Biochimica et Biophysica Acta, 2017, vol. 1863, pp. 1991-2000 (10 pages total).

Michele Cavalera et al., Obesity, metabolic dysfunction and cardiac fibrosis: pathophysiologic pathways, molecular mechanisms and therapeutic opportunities, Translational Research, 2014, doi: 10.1016/j.trsl.2014.05.001 (36 pages total).

Hong-Jun Chen et al., "Actein ameliorates hepatic steatosis and fibrosis in high fat diet-induced NAFLD by regulation of insulin and leptin resistant", Biomedicine & Pharmacotherapy, 2018, vol. 97, pp. 1386-1396 (11 pages total).

A. De Vries et al., "High-fat feeding redirects cytokine responses and decreases allergic airway eosinophilia", Clinical & Experimental Allergy, 2009, vol. 39, pp. 731-739 (9 pages total).

Stefan Fichtner-Feigl et al., "IL-13 signaling through the IL-13α2 receptor is involved in induction of TGF-β1 production and fibrosis", Nature Medicine, 2006, vol. 12, No. 1, pp. 99-106 (9 pages total).

Xiao Na Ge et al., "High-fat diet promotes lung fibrosis and attenuates airway eosinophilia after exposure to cockroach allergen in mice", Exp Lung Res., 2013, vol. 39, No. 9, pp. 365-378 (21 pages total).

Meilin Hu et al., "The Role of Berberine in the Prevention of HIF-1α Activation to Alleviate Adipose Tissue Fibrosis in High-Fat-Diet-Induced Obese Mice", Evidence-Based Complementary and Alternative Medicine, 2018, vol. 2018, Article ID 4395137, pp. 1-12 (13 pages total).

Alfred J. Kaltman et al., "Role of Circulatory Congestion in the Cardiorespiratory Failure of Obesity", The American Journal of Medicine, 1976, vol. 60, pp. 645-653 (9 pages total).

In Hee Kim et al., "Aging increases the susceptibility of hepatic inflammation, liver fibrosis and aging in response to high-fat diet in mice", Age, 2016, vol. 38, pp. 291-302 (12 pages total).

Ping Kong et al., "The Pathogenesis of Cardiac Fibrosis", Cell Mol Life Sci., 2014, vol. 71, No. 4, pp. 549-574 (43 pages total).

Eun-Young Kwon et al., "Luteolin Targets the Toll-Like Receptor Signaling Pathway in Prevention of Hepatic and Adipocyte Fibrosis

(56) References Cited

OTHER PUBLICATIONS and Insulin Resistance in Diet-Induced Obese Mice", Nutrients, 2018, vol. 10, No. 1415, pp. 1-17 (17 pages total).

Andoni Lancha et al., "Osteopontin Deletion Prevents the Development of Obesity and Hepatic Steatosis via Impaired Adipose Tissue Matrix Remodeling and Reduced Inflammation and Fibrosis in Adipose Tissue and Liver in Mice", PLoS One, 2014, vol. 9, Issue 5, e98398, pp. 1-15 (15 pages total).

Chun Geun Lee et al., "Interleukin-13 Induces Tissue Fibrosis by Selectively Stimulating and Activating Transforming Growth Factor β1", J. Exp. Med., 2001, vol. 194, No. 6, pp. 809-821 (13 pages total).

Wei Li et al., "Folic acid prevents cardiac dysfunction and reduces myocardial fibrosis in a mouse model of high-fat diet-induced obesity", Nutrition & Metabolism, 2017, vol. 14, No. 68, pp. 1-8 (8 pages total).

International Search Report of PCT/KR2020/004354 dated Jul. 17, 2020 [PCT/ISA/210].

Tsuburai et al., "Adenovirus-Mediated Transfer and Overexpression of Heme Oxygenase 1 cDNA in Lung Prevents Bleomycin-Induced Pulmonary Fibrosis via a Fas-Fas Ligand-Independent Pathway," Human Gene Therapy, 2002, vol. 13, pp. 1945-1960.

International Search Report issued Aug. 28, 2019 in International Application No. PCT/US2019/038391.

International Preliminary Report on Patentability issued Jan. 12, 2021 in International Application No. PCT/US2019/038391.

"AKI: Mechanisms—Primary Injury and Repair—II", J Am Soc Nephrol: Kidney Week Edition (Abstract Supplement), 2019, vol. 30, p. 786 (1 page).

Kwang Bon Koo, et al., "Protective Effect of Cyclo(His-Pro) on Streptozotocin-Induced Cytotoxicity and Apoptosis In Vitro", J. Microbiol. Biotechnol., 2011, vol. 21, No. 2, pp. 218-227.

Zhang et al., "Strategies for preventing peritoneal fibrosis in peritoneal dialysis patients: new insights based on peritoneal inflammation and angiogenesis", Front. Med., 2017, vol. 11, No. 3, pp. 349-358 (10 pages total).

Extended European Search Report dated Jan. 16, 2023 from the European Patent Office in EP Application No. 20776685.8.

Tim D. Hewitson, "Renal tubulointerstitial fibrosis: common but never simple", Am J Physiol Renal Physiol, Jan. 7, 2009, vol. 296, pp. F1239-F1244 (6 pages total).

Anonymous, "Retraction: Cyclo(His-Pro) up-regulates heme oxygenase 1 via activation of Nrf2-ARE signalling", J Neurochem, 2023, vol. 166(3), pp. 634 (2 pages total) (Abstract).

Anonymous, "Anatomy of the Urinary System", Hopkins Medicine, https://www.hopkinsmedicine.org/health (7 pages), accessed 2025.

* cited by examiner

USE OF CYCLO(HIS-PRO) (CHP) FOR PREVENTING, ALLEVIATING OR TREATING PERITONEAL FIBROSIS

CROSS REFERENCE TO RELATED APPLICATIONS

This application is a National Stage of International Application No. PCT/KR2020/004343, filed Mar. 30, 2020, claiming priority to Korean Patent Application No. 10-2019-0036269, filed Mar. 28, 2019 and Korean Patent Application No. 10-2020-0037858, filed Mar. 27, 2020.

TECHNICAL FIELD

The present invention relates to a use of cyclo(His-Pro) (CHP) for preventing, ameliorating or treating peritoneal fibrosis, and more specifically to a pharmaceutical composition for preventing or treating peritoneal fibrosis including CHP, a health functional food composition for preventing or ameliorating peritoneal fibrosis, a peritoneal dialysis solution, a method for preventing or treating peritoneal fibrosis using CHP, a method of peritoneal dialysis using CHP, a use of CHP in the preparation of a pharmaceutical composition for preventing or treating peritoneal fibrosis and/or a use of CHP in the preparation of a peritoneal dialysis solution.

BACKGROUND ART

Peritoneal dialysis is one of the representative renal replacement therapies, and it is a dialysis method using the peritoneum which is the body's own filter. However, if the function of the peritoneum, which is the only dialysis membrane, is not adequate, it has a fatal disadvantage that it cannot be sustained.

Accordingly, peritoneal fibrosis (PF) is a major cause of peritoneal structural changes and ultrafiltration disorders in patients with continuous ambulatory peritoneal dialysis (CAPD). Encapsulating peritoneal sclerosis (ESP), which is an extreme form of peritoneal fibrosis, is a representative cause that makes it difficult to continue peritoneal dialysis, and there is no clear preventive method so far, and it is impossible to return to normal function due to the nature of fibrosis-sclerosis. For this reason, once diagnosed, it has a very fatal course.

As such, attempts to inhibit peritoneal fibrosis in patients with kidney disease not only inhibit the progression to chronic kidney disease which causes socio-economic losses, but are also recognized as an important issue that can determine the continuity of renal replacement therapy, and there is an urgent need to develop a therapeutic agent therefor.

Meanwhile, the epithelial-mesenchymal transition (EMT) of peritoneal mesothelial cells (PMC) and the peritoneal accumulation of extracellular matrix (ECM) proteins are major features of peritoneal fibrosis, and transforming growth factor (TGF)-β1 is known to play a key role in the development of peritoneal fibrosis.

Such EMT is known to be characterized by a decrease in the expression of E-cadherin and an accumulation of the expression of α-SMA (de novo α-smooth muscle actin). Since EMT is known to be a reversible process, inhibition of EMT can be considered as a therapeutic target to preserve peritoneal function.

Under this background, since cyclo(His-Pro) (CHP) exhibited an effect of inhibition of peritoneal epithelial-to-mesenchymal transition (EMT), inhibition of peritoneal apoptosis or inhibition of immune cell infiltration into the peritoneum in an animal model in which peritoneal fibrosis was induced, the inventors of the present invention confirmed that peritoneal fibrosis can be effectively treated and thereby completed the present invention.

Meanwhile, Korean Patent Laid-Open No. 10-2013-0006170 discloses a composition for regulating blood sugar, including a soybean hydrolyzate containing cyclo(His-Pro) (CHP) at a high concentration, but the anti-fibrotic effect of CHP is not known.

DISCLOSURE

Technical Problem

An object of the present invention is to provide a pharmaceutical composition for preventing or treating peritoneal fibrosis, including cyclo(His-Pro).

Another object of the present invention is to provide a health functional food composition for preventing or ameliorating peritoneal fibrosis, including cyclo(His-Pro).

Still another object of the present invention is to provide a peritoneal dialysis solution, including cyclo(His-Pro).

Still another object of the present invention is to provide a method for preventing or treating peritoneal fibrosis, using cyclo(His-Pro).

Another object of the present invention is to provide a method of peritoneal dialysis, using cyclo(His-Pro).

Still another object of the present invention is to provide a use of cyclo(His-Pro) in the preparation of a pharmaceutical composition for preventing or treating peritoneal fibrosis.

Another object of the present invention is to provide a use of cyclo(His-Pro) in the preparation of a peritoneal dialysis solution.

Technical Solution

In order to solve the aforementioned problems, the present invention provides a pharmaceutical composition for preventing or treating peritoneal fibrosis, including cyclo (His-Pro) or a pharmaceutically acceptable salt thereof.

In addition, the present invention provides a health functional food composition for preventing or ameliorating peritoneal fibrosis, including cyclo(His-Pro) or a sitologically acceptable salt thereof.

In addition, the present invention provides a peritoneal dialysis solution, including cyclo(His-Pro) or a pharmaceutically acceptable salt thereof.

Additionally, the present invention provides a method for preventing or treating peritoneal fibrosis, including administering an effective amount of cyclo(His-Pro) to a subject in need thereof.

In addition, the present invention provides a method of peritoneal dialysis, including administering an effective amount of cyclo(His-Pro) to a subject in need thereof.

In addition, the present invention provides a use of cyclo(His-Pro) in the preparation of a pharmaceutical composition for preventing or treating peritoneal fibrosis.

In addition, the present invention provides a use of cyclo(His-Pro) in the preparation of a peritoneal dialysis solution.

According to a preferred exemplary embodiment of the present invention, the peritoneal fibrosis may include any one or more selected from the group consisting of retroperitoneal fibrosis and encapsulating peritoneal sclerosis.

According to another preferred exemplary embodiment of the present invention, cyclo(His-Pro) or a pharmaceutically acceptable salt thereof may exhibit any one or more effect selected from the group consisting of inhibition of peritoneal epithelial-to-mesenchymal transition (EMT), inhibition of peritoneal apoptosis and inhibition of immune cell infiltration into the peritoneum.

According to still another preferred exemplary embodiment of the present invention, peritoneal fibrosis may be caused by dialysis.

Advantageous Effects

Since the composition including cyclo(His-Pro) according to the present invention exhibits an effect of inhibition of epithelial-to-mesenchymal transition (EMT) in the peritoneum in which fibrosis is induced, inhibition of apoptosis or inhibition of immune cell infiltration to the peritoneum, it can effectively prevent, ameliorate or treat peritoneal fibrosis.

BEST MODE

Figure 1:
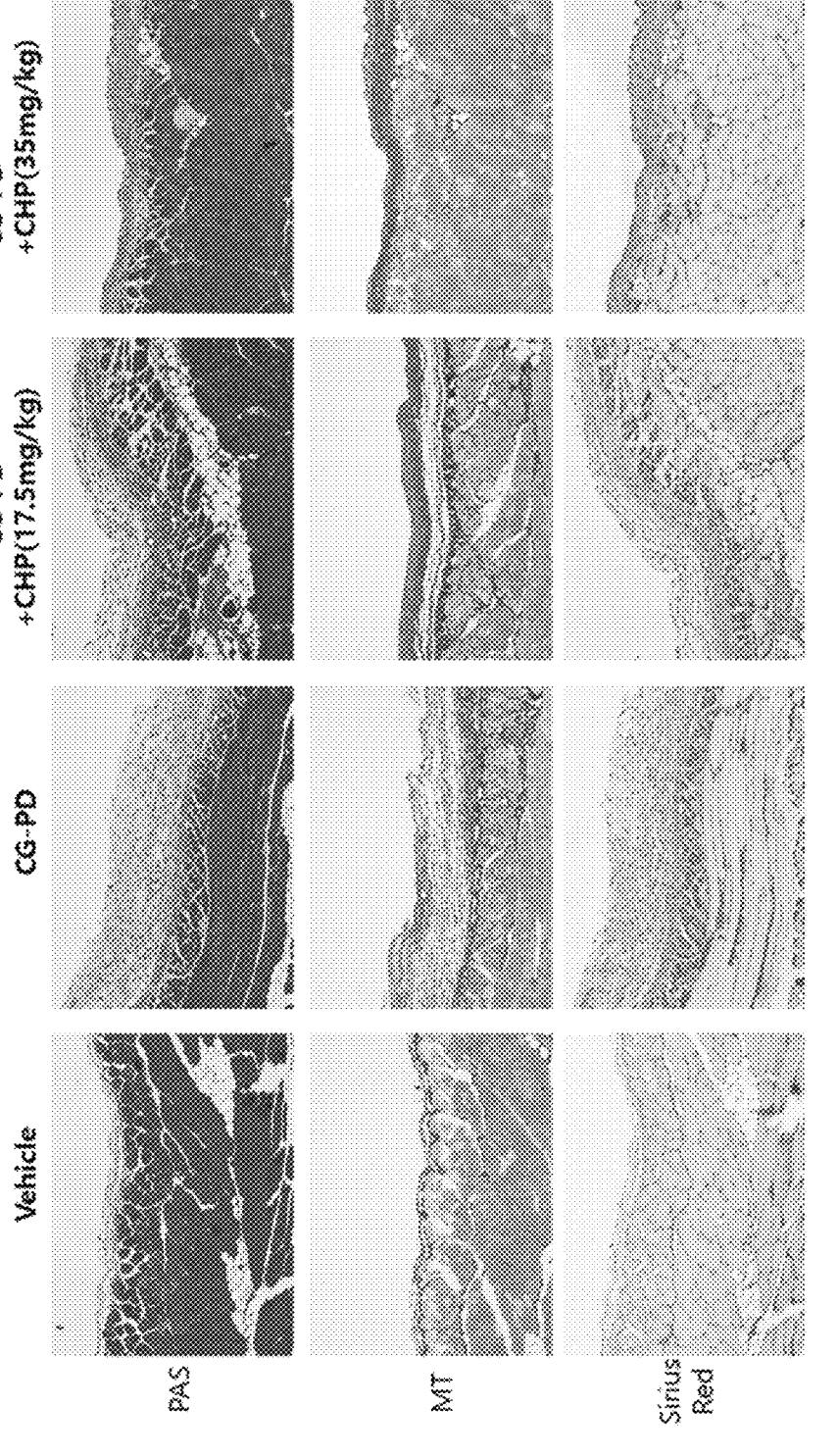
FIG. 1 is a set of photographs confirming the degree of fibrosis by staining the peritonea of animal models of peritoneal fibrosis administered with CHP (17.5 and 35 mg/kg, respectively) with the periodic acid Schiff (PAS), Masson's Trichrome (MT) and Sirius red, respectively.

Hereinafter, the present invention will be described in more detail.

As described above, attempts to inhibit peritoneal fibrosis in patients with renal disease not only inhibit the progression to chronic kidney disease which causes socio-economic losses, but are also recognized as an important issue that can determine the continuity of renal replacement therapy, and thus, there is an urgent need to develop a therapeutic agent therefor.

Accordingly, since cyclo(His-Pro) (CHP) exhibited an effect of inhibition of peritoneal epithelial-to-mesenchymal transition (EMT), inhibition of peritoneal apoptosis or inhibition of immune cell infiltration into the peritoneum in an animal model in which peritoneal fibrosis was induced, the inventors of the present invention confirmed that peritoneal fibrosis can be effectively treated and thereby completed the present invention.

Accordingly, the present invention provides a pharmaceutical composition for preventing or treating peritoneal fibrosis, including cyclo(His-Pro) or a pharmaceutically acceptable salt thereof and/or a health functional food composition for preventing or ameliorating peritoneal fibrosis, including cyclo(His-Pro) or a sitologically acceptable salt thereof.

As used herein, the term "cyclo(His-Pro) (CHP)" refers to a naturally occurring circular dipeptide composed of histidine-proline, which is a metabolite of thyrotropin-releasing hormone (TRH) or a physiologically active dipeptide that is also synthesized in the body through TRH metabolism de novo, and it refers to a substance widely distributed in the brain, spinal cord, gastrointestinal tract and the like.

In the composition of the present invention, the CHP may be synthesized or commercially obtained and used. In addition, it may be used after purification from substances containing CHP, for example, prostate extracts, soybean hydrolyzates or the like.

By use of the term "purified", it is intended to mean that CHP is in a concentrated form compared to a form obtainable from a natural origin such as prostate extracts. Purified ingredients may be concentrated from their natural sources or obtained through chemical synthesis methods.

As used herein, the term "peritoneal fibrosis" refers to a condition in which the peritoneum is fibrous and refers to abnormally formed fibrous cells in the peritoneum, for example, it is used in an inclusive sense for retroperitoneal fibrosis or encapsulating peritoneal sclerosis, but is not limited thereto. Fibrosis of the peritoneum may occur, for example, by dialysis In the composition for preventing, ameliorating or treating peritoneal fibrosis according to the present invention, cyclo(His-Pro), a pharmaceutically acceptable salt thereof or a sitologically acceptable salt thereof may exhibit any one or more effect selected from the group consisting of inhibition of peritoneal epithelial-to-mesenchymal transition (EMT), inhibition of peritonea apoptosis and inhibition of immune cell infiltration into the peritoneum.

As used herein, the term "epithelial-to-mesenchymal transition (EMT)" refers to phenotypic transformation of epithelial cells into mesenchymal cells. Specifically, EMT refers to a phenomenon in which tissue acquires motility as intercellular bonds are loosened and the cytoskeleton is changed, and cells lose their original cell phenotype and are converted to a phenotype of mesenchymal cells. Induction of EMT may lead to accumulation of fibroblasts, and induction of EMT is recognized as an important mechanism of peritoneal fibrosis.

Accordingly, in a specific exemplary embodiment of the present invention, the anti-fibrotic effect was evaluated by confirming the expression change of EMT markers such as E-cadherin and α-smooth muscle actin (α-SMA) according to CHP administration in an animal model of peritoneal fibrosis. As confirmed in FIGS. 3a, 3c and 4c, it can be seen that CHP suppresses the expression of αSMA, which is a marker of fibrosis, in the peritoneal tissue and increases the expression of E-cadherin, which is a cell junction marker, and as a result, it exhibits an anti-fibrotic effect by suppressing EMT of the peritoneum.

In another specific exemplary embodiment of the present invention, in order to evaluate peritoneal apoptosis according to CHP administration in an animal model in which peritoneal fibrosis was induced, changes in the expressions of p16 and p21, which are apoptosis markers, were confirmed. As confirmed in FIGS. 3a, 3d, 3e and 4b, the expressions of p16 and p21 in the CHP-treated group were significantly reduced, and it was found that apoptosis was suppressed.

The term "fibrosis" refers to a condition, disease or disorder characterized by dysregulated proliferation or activity of fibroblasts, abnormal accumulation of fibronectin and/or pathological or excessive accumulation of collagenous tissue.

Accordingly, in still another specific exemplary embodiment of the present invention, the anti-fibrotic effect was evaluated by confirming the change in the expression of collagen 1 according to CHP administration in an animal model in which peritoneal fibrosis was induced. As confirmed in FIGS. 1 (result of Sirius red staining), 3a, 3b and 4a, CHP significantly reduced the expression of collagen 1 increased by induction of fibrosis, and it can be seen that it exhibits an excellent anti-fibrotic effect.

In still another specific exemplary embodiment of the present invention, the therapeutic effect on peritoneal fibrosis was evaluated by confirming the degree of infiltration of immune cells according to CHP administration in an animal model in which peritoneal fibrosis was induced. As confirmed in FIGS. 1 (result of PAS staining) and 2, CHP reduced the deposition of immune cells increased by induction of fibrosis in a concentration-dependent manner, reduced the expression level of intercellular adhesion molecule 1 (ICAM-1) which causes initial immune responses, and reduced the expression level of f4/80-positive cells, which are markers of macrophages and dendritic cells, thereby drastically reducing the infiltration of immune cells. From this, it can be seen that CHP interferes with the progression of peritoneal fibrosis by reducing the infiltration of immune cells.

In the composition for preventing, ameliorating or treating peritoneal fibrosis according to the present invention, the terms "prevention". "amelioration" and/or "treatment" refer to all actions that inhibit or delay the onset of a disease or condition, all actions that ameliorate or beneficially alter the state of a disease or condition, and all actions that delay, interrupt or reverse the progression of a disease or condition.

As used herein, the term "pharmaceutically acceptable" means that it is physiologically acceptable and does not typically produce an allergic or similar reaction when administered to humans, and as the salt, an acid addition salt formed with a pharmaceutically acceptable free acid is preferred.

The pharmaceutically acceptable salt may be an acid addition salt formed using an organic or inorganic acid, and the organic acid includes, for example, formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranilic acid, dichloroacetic acid, aminooxyacetic acid, benzenesulfonic acid, p-toluenesulfonic acid or methanesulfonic acid. The inorganic acid includes, for example, hydrochloric acid, hydrobromic acid, sulfuric acid, phosphoric acid, nitric acid, carbonic acid or boric acid. The acid addition salt may preferably be in the form of a hydrochloride salt or an acetate salt, and more preferably, in the form of a hydrochloride salt.

In addition to the above, the additionally possible salt form includes a GABA salt, a gabapentin salt, a pregabalin salt, a nicotinate salt, an adipate salt, a hemimalonate, a cysteine salt, an acetylcysteine salt, a methionine salt, an arginine salt, a lysine salt, an ornithine salt, an aspartate salt or the like.

In addition, the pharmaceutical composition of the present invention may further include a pharmaceutically acceptable carrier. The pharmaceutically acceptable carrier may further include, for example, a carrier for oral administration or a carrier for parenteral administration. Carriers for oral administration may include lactose, starch, cellulose derivatives, magnesium stearate, stearic acid and the like. Carriers for parenteral administration may include water, suitable oil, saline, aqueous glucose, glycol and the like. In addition, it may further include stabilizers and preservatives. Suitable stabilizers include antioxidants such as sodium bisulfite, sodium sulfite or ascorbic acid. Suitable preservatives include benzalkonium chloride, methyl- or propyl-paraben and chlorobutanol. As other pharmaceutically acceptable carriers, reference may be made to those described in the following document (*Remington's Pharmaceutical Sciences,* 19th ed., Mack Publishing Company, Easton, PA, 1995).

The pharmaceutical composition of the present invention may be administered in any manner to mammals, including humans. For example, it may be administered orally or parenterally, and parenteral administration may be intravenous, intramuscular, intraarterial, intramedullary, intrathecal, intracardiac, transdermal, subcutaneous, intraperitoneal, intranasal, enteral, topical, sublingual or rectal administration, but is not limited thereto.

The pharmaceutical composition of the present invention may be formulated into a preparation for oral administration or parenteral administration according to the administration route as described above. When formulated, it may be formulated with one or more buffering agents (e.g., saline or PBS), carbohydrates (e.g., glucose, mannose, sucrose, or dextran, etc.), antioxidants, bacteriostats, chelating agents (e.g., EDTA or glutathione), fillers, extenders, binders, adjuvants (e.g., aluminum hydroxide), suspending agents, thickening agents, wetting agents, disintegrating agents or surfactants, diluents or excipients.

Solid preparations for oral administration include tablets, pills, powders, granules, liquids, gels, syrups, slurries, suspensions or capsules, and such solid preparations may be prepared by mixing the pharmaceutical composition of the present invention with at least one or more excipients such as starch (including corn starch, wheat starch, rice starch, potato starch, etc.), calcium carbonate, sucrose, lactose, dextrose, sorbitol, mannitol, xylitol, erythritol, maltitol, cellulose, methyl cellulose, sodium carboxymethylcellulose, hydroxypropylmethyl-cellulose, gelatin or the like. For example, tablets or sugar tablets may be obtained by blending the active ingredient with a solid excipient, grinding it, and processing it into a granule mixture after adding suitable adjuvants.

Lubricants such as magnesium stearate talc are also used in addition to simple excipients. Liquid formulations for oral use include suspensions, solutions, emulsions, syrups or the like, and various excipients, for example, wetting agents, sweetening agents, fragrances, preservatives or the like may be included, in addition to water or liquid paraffin which are commonly used simple diluents.

In addition, in some cases, cross-linked polyvinylpyrrolidone, agar, alginic acid, sodium alginate or the like may be added as a disintegrant, and an anti-aggregating agent, a lubricant, a wetting agent, a flavoring agent, an emulsifying agent, a preservative agent and the like may be further included.

For parenteral administration, the pharmaceutical composition of the present invention may be formulated in the form of an injection, a transdermal administration agent and a nasal inhalation agent together with suitable parenteral carriers according to methods known in the art. The injection must be sterilized and protected from contamination of microorganisms such as bacteria and fungi. Examples of suitable carriers for injection may be solvents or dispersion media including water, ethanol, polyols (e.g., glycerol, propylene glycol, liquid polyethylene glycol, etc.), mixtures thereof and/or vegetable oils, but are not limited thereto. More preferably, as suitable carriers, Hanks' solution, Ringer's solution, phosphate buffered saline (PBS) containing triethanolamine or isotonic solutions such as sterile water for injection, 10% ethanol, 40% propylene glycol, 5% dextrose and the like may be used. In order to protect the injection from microbial contamination, various antibacterial and antifungal agents such as paraben, chlorobutanol, phenol, sorbic acid, thimerosal and the like may be further included. In addition, in most cases, the injection may further include isotonic agents such as sugar or sodium chloride.

In the case of transdermal administration agents, forms such as an ointment, cream, lotion, gel, an external solution, a paste preparation, a liniment, aerosol and the like are included. In the above, the term 'transdermal administration' means that an effective amount of the active ingredient contained in the pharmaceutical composition is delivered into the skin by topically administering the pharmaceutical composition to the skin.

In the case of inhalation administration agents, the compound used in accordance with the present invention may be conveniently delivered in the form of an aerosol spray from a pressurized pack or a nebulizer, with the use of a suitable propellant such as dichlorofluoromethane, trichlorofluoromethane, dichlorotetrafluoroethane, carbon dioxide or other suitable gas. In the case of a pressurized aerosol, the dosage unit may be determined by providing a valve to deliver a measured amount. For example, gelatin capsules and cartridges used in inhalers or insufflators may be formulated to contain a powder mixture of the compound and a suitable powder base such as lactose or starch. Formulations for parenteral administration are described in the following document which is a commonly known prescription in all of pharmaceutical chemistry (*Remingion's Pharmaceutical Science,* 15th Edition, 1975. Mack Publishing Company, Easton, Pennsylvania 18042, Chapter 87: Blaug, Seymour).

When the pharmaceutical composition of the present invention includes cyclo(His-Pro) in an effective amount, it is possible to provide a desirable preventive, ameliorating or therapeutic effect of peritoneal fibrosis. As used herein, the term "effective amount" refers to an amount that exhibits a response greater than that of a negative control, and preferably refers to an amount sufficient to prevent, ameliorate or treat peritoneal fibrosis. The pharmaceutical composition of the present invention may include 0.01 to 99.9% of cyclo(His-Pro), and the remaining amount may be occupied by a pharmaceutically acceptable carrier. The effective amount of cyclo(His-Pro) included in the pharmaceutical composition of the present invention may vary depending on the form in which the composition is commercialized.

The total effective amount of the pharmaceutical composition of the present invention may be administered to a patient in a single dose, or may also be administered by a fractionated treatment protocol in which multiple doses are administered over a long period of time. The pharmaceutical composition of the present invention may have a varied content of the active ingredient depending on the severity of the disease. For example, it may be administered in a single dose to several divided doses such that it is preferably administered in an amount of 0.001 to 100 mg/kg of body weight per day or more preferably, 0.01 to 10 mg/kg of body weight per day, based on cyclo(His-Pro). However, for the dose of the cyclo(His-Pro), the effective dose for a patient is determined by considering various factors such as the patient's age, body weight, health status, gender, severity of the disease, diet and excretion rate, as well as the route of administration and number of treatments of the pharmaceutical composition, and thus, one of ordinary skill in the art will be able to determine the appropriate effective dose of the cyclo(His-Pro) according to the particular use for preventing, treating or ameliorating peritoneal fibrosis. The pharmaceutical composition according to the present invention is not particularly limited in its formulation, administration route and administration method as long as it shows the effects of the present invention.

The pharmaceutical composition for preventing or treating peritoneal fibrosis according to the present invention may be used alone or in combination with methods using surgery, radiation therapy, hormone therapy, chemotherapy or a biological response modifier.

As used herein, the term "health functional food" includes both the meanings of "functional food" and "health food."

As used herein, the term "functional food" is the same term as food for special health use (FoSHU), and means a food product with high medicinal and medical effects, which is processed to efficiently exhibit bioregulatory functions in addition to nutrition supply.

As used herein, the term "health food" refers to food having an active health maintenance or effect as compared with general food, and health supplement food refers to food for the purpose of health supplementation. In some cases, the terms of functional food, health food and health functional food are interchangeably used. The food may be prepared in various forms such as tablets, capsules, powders, granules, liquids, pills and the like.

As a specific example of such functional food, by using the composition, it is possible to produce processed food with improved storage properties while modifying to take into account the characteristics of agricultural products, livestock products or aquatic products.

The health functional food composition of the present invention may also be prepared in the form of nutritional supplements, food additives and the like, and it is intended for consumption by mammals including humans.

This type of food compositions may be prepared in various forms according to conventional methods known in the art. As general food, cyclo(His-Pro) may be added to produce beverages (including alcoholic beverages), fruit and processed food thereof (e.g., canned fruit, bottled fruit, jam, marmalade, etc.), fish, meat and processed food thereof (e.g., ham, sausage, corned beef, etc.), bread and noodles (e.g., udon, soba, ramen, spaghetti, macaroni, etc.), fruit juice, various drinks, cookies, Korean hard taffy, dairy products (e.g., butter, cheese, etc.), edible vegetable oils and fats, margarine, vegetable proteins, retort food, frozen food, various seasonings (e.g., soybean paste, soy sauce, sauce, etc.) and the like, but is not limited thereto.

In addition, as nutritional supplements, cyclo(His-Pro) may be added to produce capsules, tablets, pills and the like, but is not limited thereto.

In addition, as health functional food, for example, the cyclo(His-Pro) may be prepared in the form of tea, juice and drink and consumed by liquefying, granulating, encapsulating and powdering such that it may be ingested (health drink), but is not limited thereto. Also, in order to use the cyclo(His-Pro) in the form of food additives, it may be prepared and used in the form of powder or a concentrate. In addition, the cyclo(His-Pro) may be mixed with a known active ingredient known to be effective in preventing or ameliorating peritoneal fibrosis, and prepared in the form of a composition.

When the food composition of the present invention is used as a health beverage composition, the health beverage composition may contain various flavoring agents, natural carbohydrates or the like as additional components, as in conventional beverages. The aforementioned natural carbohydrates may be monosaccharides such as glucose and fructose; disaccharides such as maltose and sucrose; polysaccharides such as dextrin and cyclodextrin; sugar alcohols such as xylitol, sorbitol, erythritol and the like. As sweetening agents, natural sweetening agents such as thaumatin and stevia extract; synthetic sweeteners such as saccharin, aspartame and the like may be used. The proportion of such natural carbohydrates is generally about 0.01 to 0.04 g, preferably about 0.02 to 0.03 g per 100 mL of the composition of the present invention.

Cyclo(His-Pro) may be contained as an active ingredient in a food composition for preventing or ameliorating peritoneal fibrosis, and the amount is an effective amount to obtain the preventive or ameliorating effect, for example, it is preferably 0.01 to 100 wt. % based on the total weight of the entire composition, but is not particularly limited thereto. The food composition of the present invention may be prepared by mixing cyclo(His-Pro) with other active ingredients known to be effective in preventing or ameliorating peritoneal fibrosis.

In addition to the above, the health functional food of the present invention may contain various nutrients, vitamins, electrolytes, flavoring agents, coloring agents, pectic acid, salts of pectic acid, alginic acid, salts of alginic acid, organic acids, protective colloid thickeners, pH regulators, stabilizers, antiseptics, glycerin, alcohols, carbonating agents or the like. In addition, the health food of the present invention may contain fruit flesh for the production of natural fruit juice, fruit juice beverages, or vegetable beverages. These components may be used independently or in combination. The proportion of these additives is not critically important, but is generally chosen in a range from 0.01 to 0.1 parts by weight per 100 parts by weight of the composition of the present invention.

Since cyclo(His-Pro) or a pharmaceutically acceptable salt thereof of the present invention inhibits EMT and apoptosis of peritoneal cells, it may be included in a peritoneal dialysis solution to ameliorate, delay, prevent or treat peritonea fibrosis and peritoneal fibers.

The peritoneal dialysis solution including cyclo(His-Pro) or a pharmaceutically acceptable salt thereof according to the present invention may include any one or more selected from the group consisting of an osmotic agent, a buffer, an electrolyte and a combination thereof. For example, the osmotic agent may include glucose, glucose polymers (e.g., maltodextrin and icodextrin), glucose polymer derivatives, cyclodextrins, modified starch, hydroxyethyl starch, polyols, fructose, amino acids, peptides, proteins, aminosaccharides, glycerol, N-acetyl glucosamine (NAG) or a combination thereof. The buffer may include bicarbonate, lactate, pyruvate, acetate, citrate, tris (i.e., tris(hydroxymethyl)aminomethane), amino acids, peptides or a combination thereof. The electrolyte may include sodium, potassium, magnesium, calcium and chloride.

The peritoneal dialysis solution of the present invention may include one or more dialysis components (elements or components of the dialysis solution) and a therapeutically effective amount of an active substance, and include cyclo(His-Pro) or a pharmaceutically acceptable salt thereof as a component for alleviating, ameliorating, preventing or treating peritoneal fibrosis and peritoneal fibers. The peritoneal dialysis solution may be a dialysis concentrate, and the dialysis solution may include about 0.1 μM to about 1,000 μM of cyclo(His-Pro) or a pharmaceutically acceptable salt thereof.

The peritoneal dialysis solution may be used as a single dialysis solution in a single container or as a dialysate in a separately housed or multi-chambered container, and may be administered to a patient at the same time of or by having a time difference with the conventionally used dialysis solution in peritoneal dialysis.

In addition, the present invention relates to a method for preventing or treating peritoneal fibrosis, including administering an effective amount of cyclo(His-Pro) to a subject in need thereof.

The present invention also relates to a method of peritoneal dialysis, including administering an effective amount of cyclo(His-Pro) to a subject in need thereof.

In the methods of the present invention, the term "subject" includes any animal (e.g., human, horse, pig, rabbit, dog, sheep, goat, non-human primate, cow, cat, guinea pig or rodent), but is not limited thereto. These terms do not denote a specific age or gender. Accordingly, these are intended to include adult/adult and neonatal subjects, whether female/female or male/male, as well as fetuses. A patient refers to a subject afflicted with a disease or disorder. The term "patient" includes human and veterinary subjects.

In the method for preventing or treating peritoneal fibrosis according to the present invention, the description of the composition including the effect of CHP and the administration route thereof, the number of administrations, the dosage and the like is the same as described above, and thus, the description thereof will be omitted.

The method of peritoneal dialysis according to the present invention may be performed on all patients whose kidneys are damaged and cannot excrete water and wastes on their own, and the patient may be, for example, a chronic renal failure patient, but is not limited thereto.

The method of peritoneal dialysis according to the present invention may be performed by a method known in the art, and for example, it may be carried out in a manner by inserting a catheter (conduit) leading to the abdominal cavity in the lower abdomen and inserting a dialysis solution therethrough to remove moisture and wastes from the body's waste products and water through diffusion and penetration into the dialysis solution, but is not limited thereto.

Furthermore, the present invention provides a use of cyclo(His-Pro) in the preparation of a pharmaceutical composition for preventing or treating peritoneal fibrosis.

In addition, the present invention provides a use of cyclo(His-Pro) in the preparation of a peritoneal dialysis solution.

In the uses of the present invention, the description of the effect of CHP, the pharmaceutical composition for preventing or treating peritoneal fibrosis, and the peritoneal dialysis solution are the same as described above, and thus, the description thereof will be omitted.

Hereinafter, the present invention will be described in more detail through examples. However, since the present invention may have various changes and forms, the specific examples and descriptions described below are only for helping the understanding of the present invention and are not intended to limit the present invention to a specific disclosed form. It should be understood that the scope of the present invention includes all modifications, equivalents and substitutes included in the spirit and scope of the present invention.

Modes of the Invention

Preparation Example

Cyclo(His-Pro) (CHP) used in the following examples was purchased from Bachem and used.

Example 1

Confirmation of the Protective Effect on Peritoneal Sclerosis in Animal Model of Peritoneal Fibrosis by CHP Administration
1-1. Administration of CHP and Negative Controls in Animal Model of Peritoneal Fibrosis
In order to create an animal model of peritoneal fibrosis, 7-week-old C57BL/6 male mice were purchased from Koatech and bred under constant conditions (temperature: 22±2° C., relative humidity: 55±10%, circadian cycle: 12 hours). Five animals were grouped into one group, and water and food were freely supplied in cages, and they were used in the experiment after acclimatization for one week before the experiment. After the acclimatization period, 0.1% chlorohexidine was administered by intraperitoneal injection every 3 days for 30 days to establish an animal model of peritoneal fibrosis. Divided into 4 groups, Group 1 of the experimental animals was set as a control group (vehicle) that did not undergo peritoneal fibrosis by administering phosphate-buffered saline, and Group 2 was set as a control group (CG-PD) in which peritoneal fibrosis was progressed by administering phosphate-buffered saline. Group 3 was orally administrated with CHP at a concentration of 17.5 mg/kg (CG-PD+CHP(17.5)), and Group 4 was orally administered with CHP at a concentration of 35 mg/kg (CG-PD+CHP (35)) through 1 mL syringes every day for 30 days.
1-2. Tissue Collection and Staining of Mouse Groups in Animal Model of Peritoneal Fibrosis
Among the experimental animals designed in Example 1-1, the peritoneum was obtained from the mice of the groups administered with the drug and 0.1% chlorohexidine for 30 days from the xyphoid process to the upper part of the pelvic cavity, and then sacrificed with whole blood. From the skin to the parietal peritoneum, the tissues of the left abdomen were excised in a size of 0.5×1.0 cm, and some were fixed in 10% formalin for immunostaining and then embedded in paraffin. The tissue sections were cut to a thickness of 4 μm and evaluated by performing Periodic acid-Schiff (PAS) staining, Masson's trichrome (MT) staining and Sirius Red staining to check the degree of peritoneal fibrosis. After observation with an optical microscope, photographs were taken (Olympus BX-50, Olympus Optical, Tokyo, Japan).
1-3. Confirmation of Anti-Fibrotic Effect in Animal Model of Peritoneal Fibrosis
As a result of the experiment, as shown in FIG. 1, it was confirmed that the deposition of immune cells was increased in the fibrosis control group (CG-PD) than in the negative control (vehicle) through PAS staining, and the deposition of immune cells was significantly reduced in a concentration-dependent manner by CHP administration. In addition, through MT staining, it was confirmed that the peritoneal layer was thicker in the fibrosis control group (CG-PD) than in the negative control group (vehicle), and the peritoneal layer which was thickened in the CHP 35 mg/kg administration group compared to the 17.5 mg/kg administration group was significantly reduced. Through Sirius red staining, it was confirmed that the accumulation of extracellular matrix (ECM) collagen was significantly reduced in a concentration-dependent manner according to the administration of CHP.
Through the above results, it was possible to confirm the excellent therapeutic effect of CHP on peritoneal fibrosis.

Example 2

Figure 2:
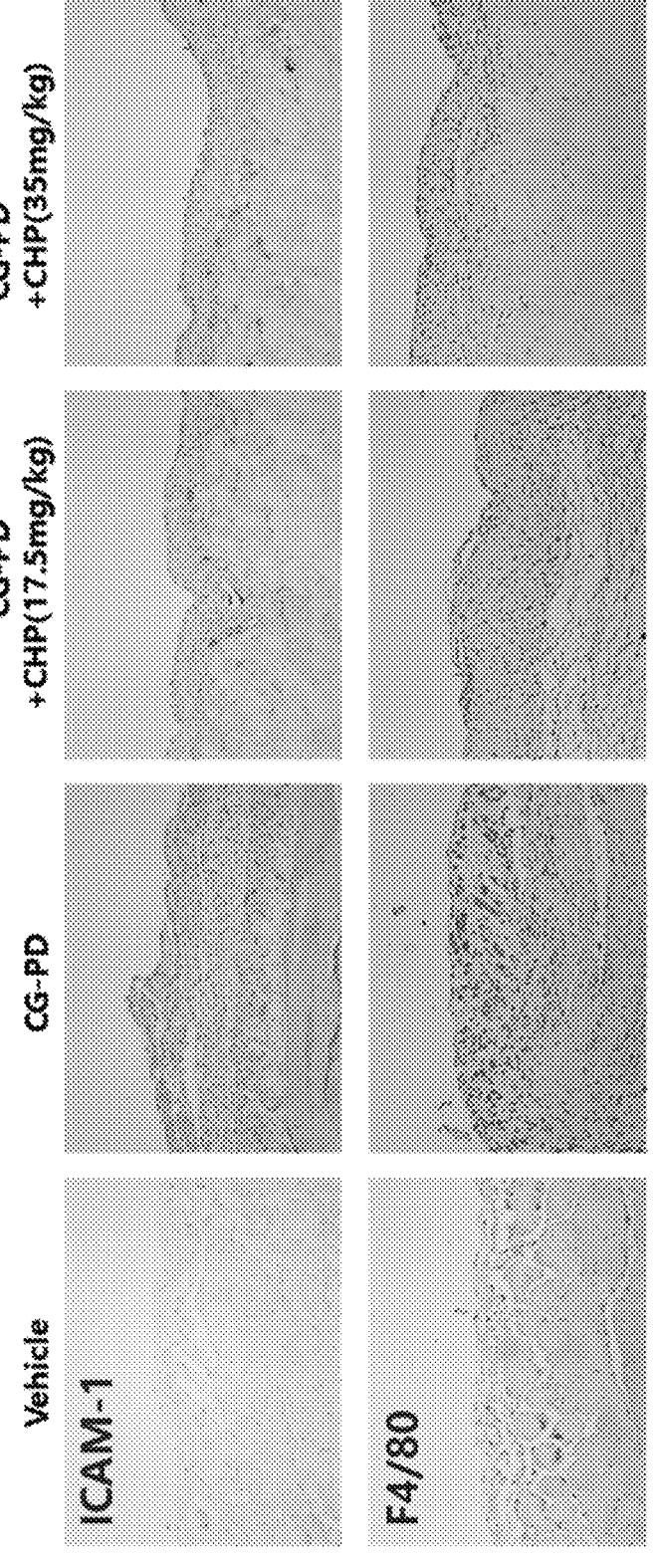
FIG. 2 is a set of photographs observing the degree of peritoneal fibrosis by confirming the protein expression levels of ICAM-1 and F4/80 in the peritonea of animal models of peritoneal fibrosis administered with CHP (17.5 and 35 mg/kg, respectively) through immunohistochemical (IHC) staining, respectively.

Confirmation of Preventive Effect on Peritoneal Sclerosis in Animal Model Of Peritoneal Fibrosis
Peritoneal tissues were extracted from the mice of each group of Example 1-1, fixed in 10% formalin for immunostaining and then embedded in paraffin. Using the streptavidin biotin peroxidase (Vector Laboratories) method, these were reacted with each of the anti-ICAM1 antibody and the anti-F40/80 antibody at 4° C. for 16 hours, followed by color development with diaminobenzidine tetrahydrochloride (DAB) to confirm the expressions. After each expression level was observed with an optical microscope, photographs were taken (Olympus BX-50, Olympus Optical, Tokyo, Japan).
As a result of the experiment, as shown in FIG. 2, it was confirmed that the expression level of intercellular adhesion molecule 1 (ICAM-1), which induces an initial immune response, was increased in the fibrosis control group (CG-PD) than in the negative control group (vehicle), and as the severity of peritoneal sclerosis decreased by CHP administration, it was confirmed that the expression level of ICAM-1 also decreased. In addition, in the CG-PD group, the expression levels of f4/80-positive cells, which are well known as markers of macrophages and dendritic cells among immune cells, increased with an increase in peritoneal sclerosis, and then it was confirmed that the infiltration of immune cells was rapidly decreased by CHP administration.
Through the above results, it was confirmed that CHP administration can inhibit the infiltration of immune cells and interfere with the progression of peritoneal sclerosis.

Example 3

Confirmation of Protein Expressions of Fibrosis Markers Collagen 1 and αSMA and Apoptosis Markers p16 and p21 in Animal Model of Peritoneal Fibrosis Administered with CHP
Isoflurane which is necessary for anesthesia and dissection of mice in each group of Example 1-1 was purchased from Hana Pharm, and VetEquip's RC2 Rodent Circuit Controller Anesthesia System was prepared. Phosphate-buffered saline (PBS) was purchased from Hyclone. In order to isolate the peritoneal tissue of the mice, the mice were anesthetized by respiratory anesthesia with 3 to 3.5% isoflurane. After blood was drawn from the heart of anesthetized mice, the peritoneal tissue was immediately removed, washed with PBS, and 50 mg of the peritoneal tissue was cut out and placed in 500 μL of RIPA buffer containing protease and phosphatase inhibitors, and it was crushed using IKA's T10 homogenizer. After standing on ice for 15 minutes, centrifugation was performed at 15000 rpm at 4° C. The supernatant was collected and the protein concentration was measured by BCA quantitation, and in the same amount of the samples, the protein was separated using the Bolt™ protein gel electrophoresis system, and then transferred to a nitrocellulose membrane. The membrane was blocked with 5% skim milk at room temperature for 1 hour, and then reacted with primary antibodies collagen 1, αSMA, NRF2, p16, p21 and GAPDH antibodies overnight at 4° C. After washing 3 times for 10 minutes with TBST, the reaction was performed with the secondary antibodies at room temperature for 1 hour. After washing 3 times for 10 minutes with TBST, the expression level was measured by reacting with ECL. The size of the appearing band was quantified using the ImageJ program, and each band size value was divided by the GAPDH band size value and corrected. Statistical significance was analyzed using Student's t-test statistical method with the peritoneal fibrosis control group (CG-PD) (*p<0.05, p<0.05, *p<0.0005).

Figure 3A:
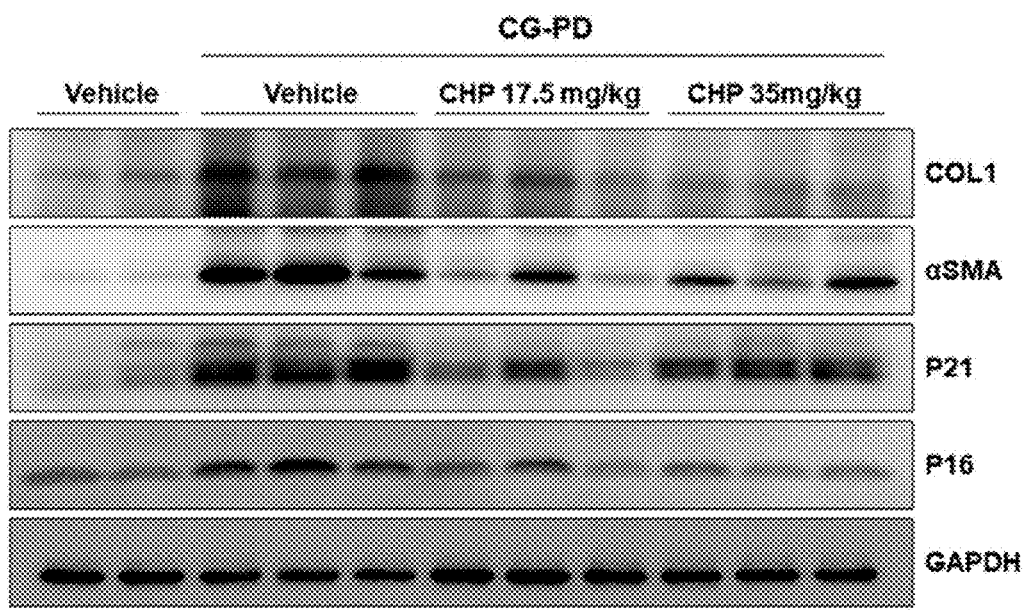
FIG. 3a shows band results confirming the changes in the protein expression levels of collagen 1 and αSMA, which are markers of fibrosis, and p16 and p21, which are apoptosis markers, in the peritoneal tissues of animal models of peritoneal fibrosis administered with CHP (17.5 and 35 mg/kg, respectively) by Western blot, and FIG. 3b (collagen 1), FIG. 3c (αSMA), FIG. 3d (p21) and FIG. 3e (p16) are results obtained by quantifying the band size of each target and showing the results as graphs.
Figure 3B:
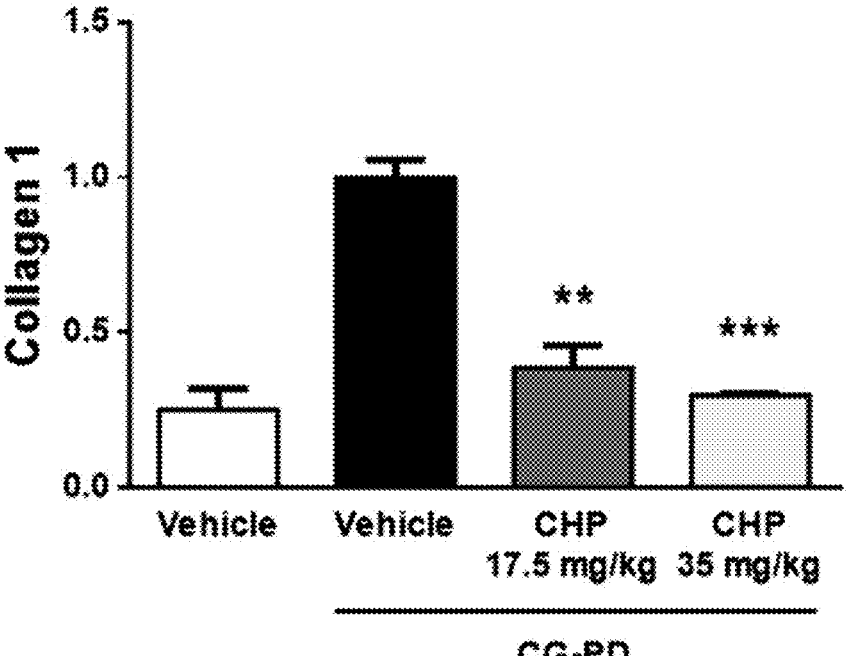
Figure 3C:
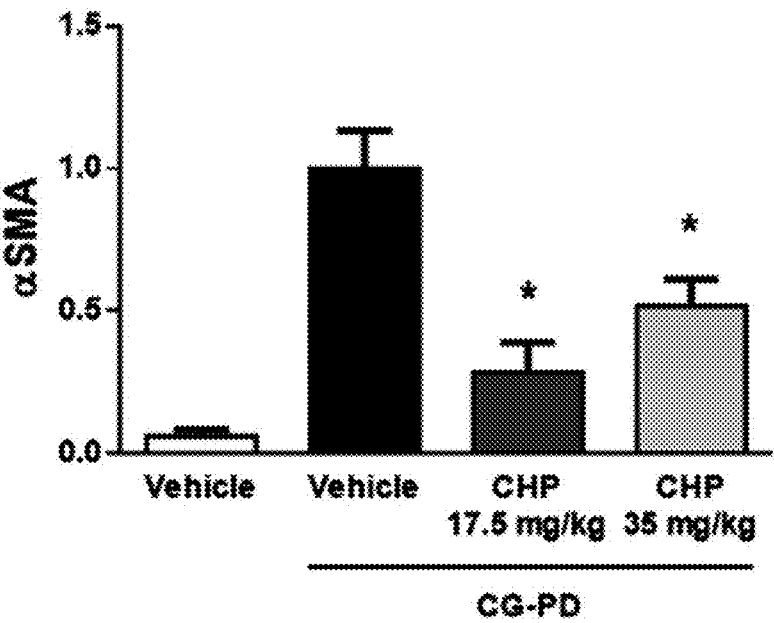
Figure 3D:
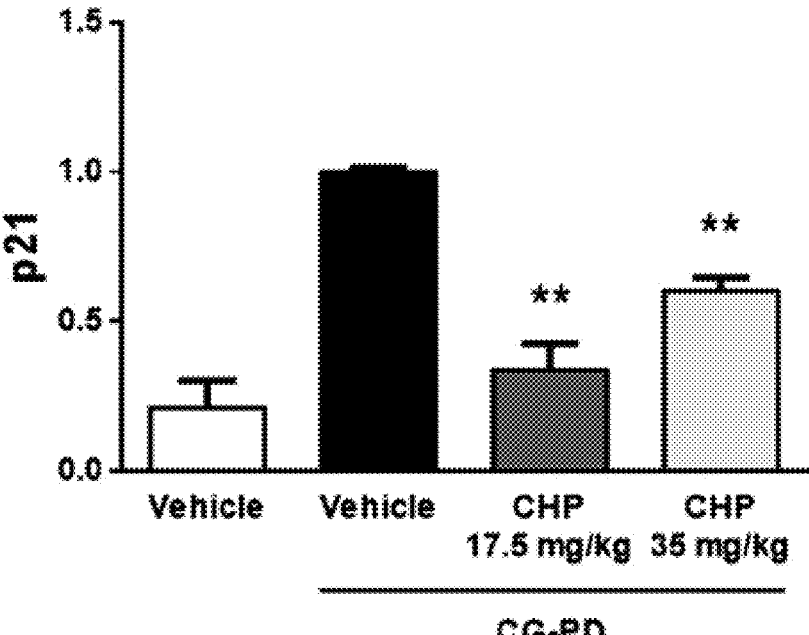
Figure 3E:
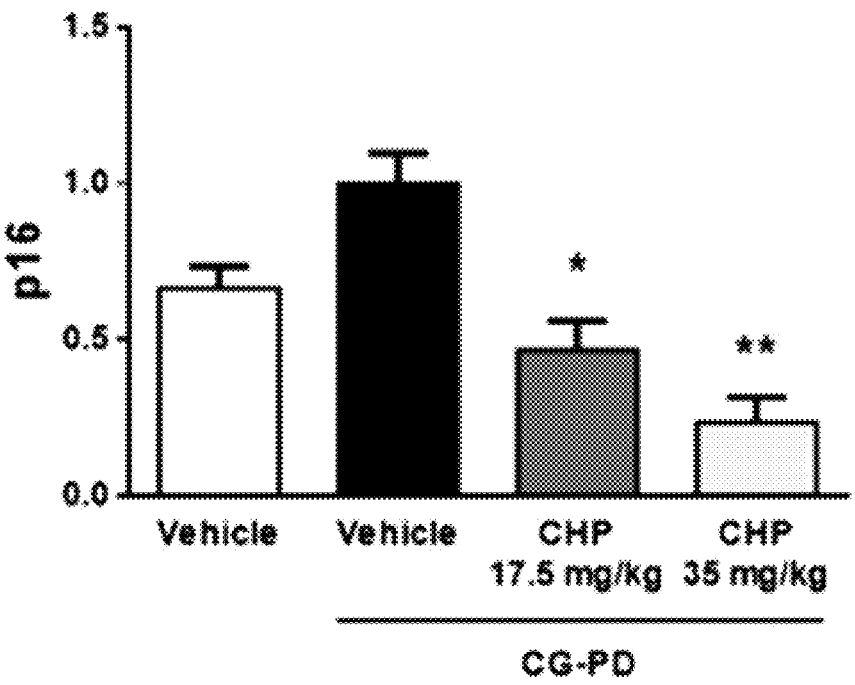

As a result of the experiment, as shown in FIGS. 3*a*, 3*b* and 3*c*, it was observed that the extracellular matrix collagen and α-SMA, which are markers of fibroblasts, were statistically significantly decreased in the CHP-administered group, and it was confirmed that the progression of peritoneal sclerosis was inhibited. In addition, as shown in FIGS. 3*a*, 3*d* and 3*e*, it was confirmed that the proteins of p16 and p21, which cause cell cycle blockade and eventually apoptosis, were significantly reduced by CHP administration.

These results mean that CHP inhibits apoptosis and ameliorates peritoneal fibrosis, and it was confirmed as a basis for application to the treatment of peritoneal fibrosis.

Example 4

Confirmation of Gene Expressions of Fibrosis Marker Collagen 1, Cell Cycle Blocking Marker p21 and Cell Junction Marker E-Cadherin in Animal Model of Peritoneal Fibrosis Administered with CHP Isoflurane which is necessary for anesthesia and dissection of mice in each group of Example 1-1 was purchased from Hana Pharma, and VetEquip's RC2 Rodent Circuit Controller Anesthesia System was prepared. Phosphate-buffered saline (PBS) was purchased from Hyclone. In order to isolate the peritoneal tissue of the mice, the mice were anesthetized by respiratory anesthesia with 3 to 3.5% isoflurane. After blood was drawn from the heart of the anesthetized mice, the peritoneal tissue was immediately removed, 50 mg of the peritoneum was cut, 500 μL of NucleoZOL was added, and then it was crushed using IKA's T10 homogenizer. Subsequently, RNA was extracted according to NucleoZOL's total RNA isolation protocol, and cDNA was synthesized from 1 μg of RNA by reverse transcription polymerase chain reaction using the iScript cDNA synthesis kit. The synthesized cDNA was analyzed by real-time PCR with iQ SYBR Green Supermix using forward/reverse primer sets corresponding to each gene. The expression value of each gene was corrected by dividing by the expression value of GAPDH, a housekeeping gene. Statistical significance was analyzed using Student's t-test statistical method with the peritoneal fibrosis control group (CG-PD) (*p<0.05, p<0.0$^5$, *p<0.0005).

Figure 4A:
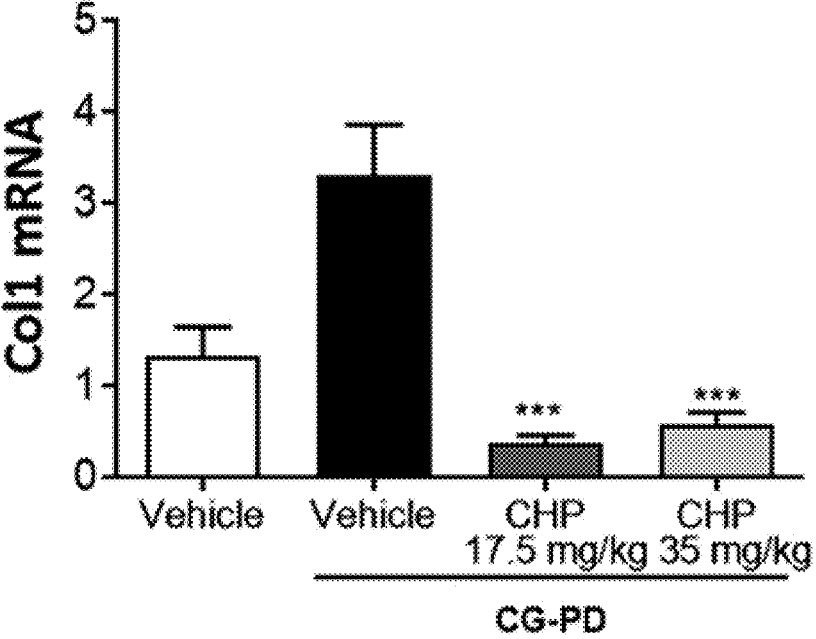
FIG. 4a is a graph confirming the change in the gene expression level of collagen 1, which is a marker of fibrosis, in the peritoneal tissue of animal models of peritoneal fibrosis administered with CHP (17.5 and 35 mg/kg, respectively)
Figure 4B:
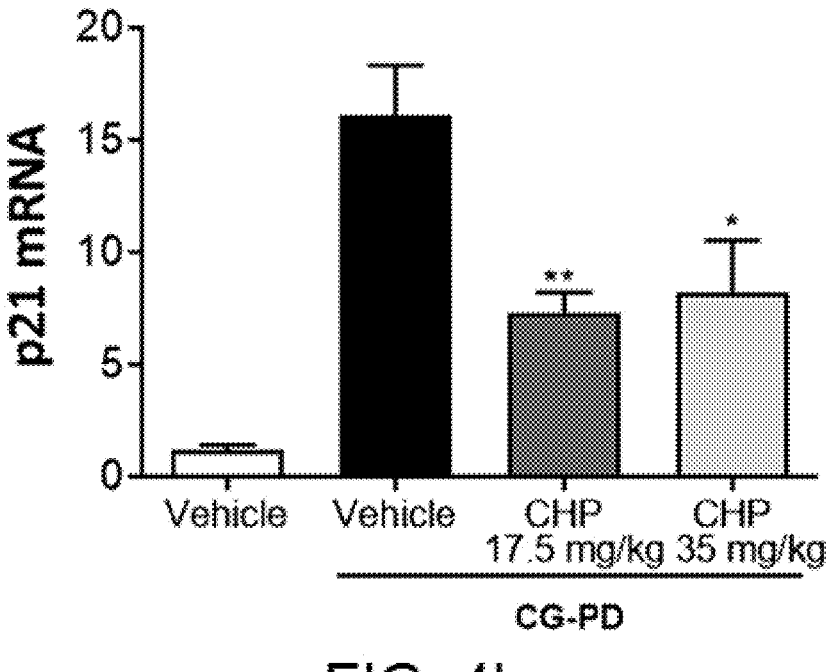
FIG. 4b is a graph confirming the change in the gene expression level of p21, which is a cell cycle blocking marker.
Figure 4C:
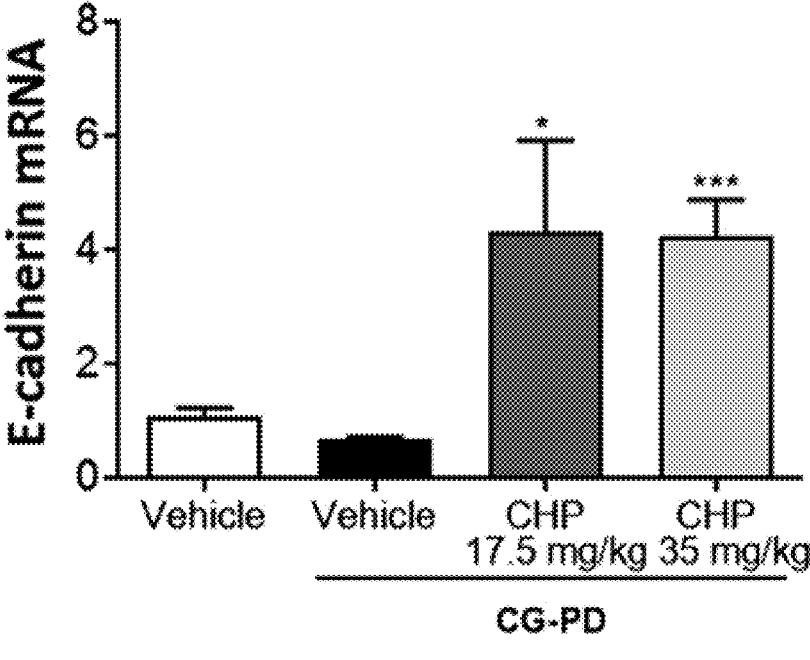
FIG. 4c is a graph confirming the change in the gene expression level of E-cadherin, which is a cell junction marker.

As a result of the experiment, as shown in FIG. 4*a*, it was confirmed that the mRNA expression of the extracellular matrix collagen 1 was decreased in the CHP-administered group. In addition, as shown in FIG. 4*b*, it was confirmed that the gene of p21, which induces cell cycle blockade and ultimately causes apoptosis, was significantly reduced by CHP administration, and as shown in FIG. 4*c*, it was confirmed that the expression level of E-cadherin, which is a cell junction marker, was significantly increased in the CHP-administered group.

These results show that CHP can prevent apoptosis and inhibit the progression of peritoneal fibrosis.

The invention claimed is:

1. A method for preventing or treating peritoneal fibrosis in a subject in need thereof, comprising administering an effective amount of cyclo(His-Pro) or a pharmaceutically acceptable salt thereof to the subject.

2. The method of claim 1, wherein the peritoneal fibrosis includes any one or more selected from the group consisting of retroperitoneal fibrosis and encapsulating peritoneal sclerosis.

3. The method of claim 1, wherein the cyclo(His-Pro) or the pharmaceutically acceptable salt thereof exhibits any one or more effect selected from the group consisting of inhibition of peritoneal epithelial-to-mesenchymal transition (EMT), inhibition of peritoneal apoptosis and inhibition of immune cell infiltration into the peritoneum.

4. The method of claim 1, wherein the peritoneal fibrosis is caused by dialysis.

5. The method of claim 1, wherein the cyclo(His-Pro) or the pharmaceutically acceptable salt thereof is administered orally or parenterally.

6. The method of claim 1, wherein the cyclo(His-Pro) or the pharmaceutically acceptable salt thereof is administered intravenously, intramuscularly, intraarterially, intrathecally, transdermally, subcutaneously, intraperitoneally, intranasally, enterally, topically, sublingually, rectally, or in an intramedullary or intracardiac route.

7. A method for preventing or treating peritoneal fibrosis in a subject in need thereof, comprising administering an effective amount of a composition comprising cyclo(His-Pro) or a pharmaceutically acceptable salt thereof to the subject, wherein the peritoneal fibrosis is epithelial-mesenchymal transition (EMT)-induced peritoneal fibrosis.

8. The method of claim 7, wherein the peritoneal fibrosis is caused by dialysis and the composition is administered in a form of peritoneal dialysis solution.

* * * * *